(12) United States Patent
Bochenko

(10) Patent No.: US 9,931,498 B2
(45) Date of Patent: Apr. 3, 2018

(54) INJECTION SITE INFORMATION CAP

(71) Applicant: CRISI Medical Systems, Inc., Franklin Lakes, NJ (US)

(72) Inventor: Walter John Bochenko, Encinitas, CA (US)

(73) Assignee: CRISI Medical Systems, Inc., Franklin Lakes, NJ (US)

( * ) Notice: Subject to any disclaimer, the term of this patent is extended or adjusted under 35 U.S.C. 154(b) by 0 days.

(21) Appl. No.: 15/352,912

(22) Filed: Nov. 16, 2016

(65) Prior Publication Data

US 2017/0056641 A1 Mar. 2, 2017

Related U.S. Application Data

(62) Division of application No. 13/802,231, filed on Mar. 13, 2013.

(51) Int. Cl.
*A61M 39/20* (2006.01)
*A61M 39/02* (2006.01)
*A61M 39/16* (2006.01)
*A61M 39/10* (2006.01)

(52) U.S. Cl.
CPC ........ *A61M 39/20* (2013.01); *A61M 39/0208* (2013.01); *A61M 39/162* (2013.01); *A61M 2039/1044* (2013.01); *A61M 2039/1077* (2013.01); *A61M 2205/502* (2013.01); *A61M 2205/52* (2013.01); *A61M 2205/6009* (2013.01); *A61M 2205/6054* (2013.01); *A61M 2205/6063* (2013.01); *A61M 2205/6072* (2013.01); *A61M 2205/6081* (2013.01); *A61M 2205/82* (2013.01)

(58) Field of Classification Search
CPC .. A61M 2039/0036; A61M 2039/1033; A61M 2039/1083; A61M 2039/1088; A61M 39/20; A61M 39/162; A61M 39/0208; A61M 2025/60; A61M 2025/6063; A61M 2025/6009; A61M 2025/6018; A61M 2025/6027; A61M 2025/6054
See application file for complete search history.

(56) References Cited

U.S. PATENT DOCUMENTS

| 614,703 A | 1/1898 | Delory |
| 3,430,625 A | 3/1969 | McLeod, Jr. |
| 4,003,252 A | 1/1977 | Dewath |
| 4,415,802 A | 11/1983 | Long |
| 4,650,475 A | 3/1987 | Smith et al. |

(Continued)

FOREIGN PATENT DOCUMENTS

| DE | 29617777 U1 | 1/1997 |
| EP | 1980974 A2 | 10/2008 |

(Continued)

*Primary Examiner* — Scott Medway
(74) *Attorney, Agent, or Firm* — The Webb Law Firm

(57) ABSTRACT

A injection site information cap includes a housing, a cover portion, an engagement portion configured to couple to and cover an injection port of an injection site, and at least one information element on the cover portion that is positioned to be automatically sensed by at least one sensor of the injection site when the engagement portion is coupled to or is being coupled to the medication injection port. Related apparatus, systems, and techniques are also described.

10 Claims, 6 Drawing Sheets

(56) References Cited

U.S. PATENT DOCUMENTS

| | | | |
|---|---|---|---|
| 4,853,521 A | 8/1989 | Claeys et al. | |
| 4,857,713 A | 8/1989 | Brown | |
| 4,921,277 A | 5/1990 | McDonough | |
| 4,978,335 A | 12/1990 | Arthur, III | |
| 5,011,032 A | 4/1991 | Rollman | |
| 5,040,422 A | 8/1991 | Frankenberger et al. | |
| 5,078,683 A | 1/1992 | Sancoff et al. | |
| 5,179,862 A | 1/1993 | Lynnworth | |
| 5,190,534 A * | 3/1993 | Kendell | A61M 39/162 604/29 |
| 5,247,826 A | 9/1993 | Frola et al. | |
| 5,279,576 A | 1/1994 | Loo et al. | |
| 5,317,506 A | 5/1994 | Coutre et al. | |
| 5,338,157 A | 8/1994 | Blomquist | |
| 5,383,858 A | 1/1995 | Reilly et al. | |
| 5,429,602 A | 7/1995 | Hauser | |
| 5,463,906 A | 11/1995 | Spani et al. | |
| 5,531,697 A | 7/1996 | Olsen et al. | |
| 5,531,698 A | 7/1996 | Olsen | |
| 5,569,212 A | 10/1996 | Brown | |
| 5,611,784 A | 3/1997 | Barresi et al. | |
| 5,612,524 A | 3/1997 | Sant'Anselmo et al. | |
| 5,628,309 A | 5/1997 | Brown | |
| 5,651,775 A | 7/1997 | Walker et al. | |
| 5,692,640 A | 12/1997 | Caulfield et al. | |
| 5,713,856 A | 2/1998 | Eggers et al. | |
| 5,720,733 A | 2/1998 | Brown | |
| 5,740,428 A | 4/1998 | Mortimore et al. | |
| 5,781,442 A | 7/1998 | Engleson et al. | |
| 5,782,814 A | 7/1998 | Brown et al. | |
| 5,792,117 A | 8/1998 | Brown | |
| 5,845,264 A | 12/1998 | Nellhaus | |
| 5,873,731 A | 2/1999 | Prendergast | |
| 5,882,338 A | 3/1999 | Gray | |
| 5,920,263 A | 7/1999 | Huttenhoff et al. | |
| 5,925,014 A | 7/1999 | Teeple, Jr. | |
| 5,941,846 A | 8/1999 | Duffy et al. | |
| 5,984,901 A | 11/1999 | Sudo et al. | |
| 6,019,745 A | 2/2000 | Gray | |
| 6,039,251 A | 3/2000 | Holowko et al. | |
| 6,106,498 A | 8/2000 | Friedli et al. | |
| 6,123,686 A | 9/2000 | Olsen et al. | |
| 6,192,945 B1 | 2/2001 | Ford et al. | |
| D438,634 S | 3/2001 | Merry | |
| 6,249,299 B1 | 6/2001 | Tainer | |
| 6,256,037 B1 | 7/2001 | Callahan | |
| 6,270,455 B1 | 8/2001 | Brown | |
| 6,277,099 B1 | 8/2001 | Strowe et al. | |
| 6,338,200 B1 | 1/2002 | Baxa et al. | |
| 6,341,174 B1 | 1/2002 | Callahan et al. | |
| 6,342,889 B1 | 1/2002 | Callahan | |
| 6,381,029 B1 | 4/2002 | Tipirneni | |
| 6,422,094 B1 | 7/2002 | Ganshorn | |
| 6,464,667 B1 | 10/2002 | Kamen et al. | |
| 6,468,424 B1 | 10/2002 | Donig et al. | |
| 6,471,089 B2 | 10/2002 | Liff et al. | |
| 6,482,185 B1 | 11/2002 | Hartmann | |
| 6,519,569 B1 | 2/2003 | White et al. | |
| 6,579,231 B1 | 6/2003 | Phipps | |
| RE38,189 E | 7/2003 | Walker et al. | |
| 6,626,355 B2 | 9/2003 | Sasse et al. | |
| 6,626,862 B1 | 9/2003 | Duchon et al. | |
| D481,121 S | 10/2003 | Evans | |
| 6,641,562 B1 | 11/2003 | Peterson | |
| 6,644,130 B2 | 11/2003 | Imai et al. | |
| 6,671,563 B1 | 12/2003 | Engelson et al. | |
| D485,356 S | 1/2004 | Evans | |
| 6,675,660 B1 | 1/2004 | Mosier et al. | |
| 6,685,227 B2 | 2/2004 | Merry et al. | |
| 6,685,678 B2 | 2/2004 | Evans et al. | |
| 6,697,067 B1 | 2/2004 | Callahan et al. | |
| 6,731,989 B2 | 5/2004 | Engleson et al. | |
| 6,733,495 B2 | 5/2004 | Bek et al. | |
| 6,742,992 B2 | 6/2004 | Davis | |
| 6,790,198 B1 | 9/2004 | White et al. | |
| 6,798,533 B2 | 9/2004 | Tipirneni | |
| 6,825,864 B2 | 11/2004 | Botten et al. | |
| 6,851,615 B2 | 2/2005 | Jones | |
| 6,854,338 B2 | 2/2005 | Khuri-Yakub et al. | |
| 6,915,170 B2 | 7/2005 | Engleson et al. | |
| 6,960,192 B1 | 11/2005 | Flaherty et al. | |
| 6,985,870 B2 | 1/2006 | Martucci et al. | |
| 6,993,402 B2 | 1/2006 | Klass et al. | |
| 7,000,485 B2 | 2/2006 | Ao et al. | |
| 7,017,623 B2 | 3/2006 | Tribble et al. | |
| 7,061,831 B2 | 6/2006 | De La Huerga | |
| 7,074,205 B1 | 7/2006 | Duffy et al. | |
| 7,074,209 B2 | 7/2006 | Evans et al. | |
| 7,096,072 B2 | 8/2006 | Engleson et al. | |
| 7,103,419 B2 | 9/2006 | Engleson et al. | |
| 7,106,479 B2 | 9/2006 | Roy et al. | |
| 7,107,106 B2 | 9/2006 | Engleson et al. | |
| 7,115,113 B2 | 10/2006 | Evans et al. | |
| 7,116,343 B2 | 10/2006 | Botten et al. | |
| 7,117,041 B2 | 10/2006 | Engleson et al. | |
| 7,161,488 B2 | 1/2007 | Frasch | |
| 7,171,277 B2 | 1/2007 | Engleson et al. | |
| 7,175,081 B2 | 2/2007 | Andreasson et al. | |
| 7,180,624 B2 | 2/2007 | Tipirneni | |
| 7,182,256 B2 | 2/2007 | Andreasson et al. | |
| 7,225,683 B2 | 6/2007 | Harnett et al. | |
| 7,236,936 B2 | 6/2007 | White et al. | |
| 7,237,199 B1 | 6/2007 | Menhardt et al. | |
| 7,264,323 B2 | 9/2007 | Tainer et al. | |
| 7,299,981 B2 | 11/2007 | Hickle et al. | |
| 7,319,540 B2 | 1/2008 | Tipirneni | |
| 7,347,841 B2 | 3/2008 | Elhadad et al. | |
| 7,358,505 B2 | 4/2008 | Woodworth et al. | |
| 7,360,448 B2 | 4/2008 | Maginnis et al. | |
| 7,364,067 B2 | 4/2008 | Steusloff et al. | |
| 7,370,797 B1 | 5/2008 | Sullivan et al. | |
| 7,375,737 B2 | 5/2008 | Botten et al. | |
| 7,384,410 B2 | 6/2008 | Eggers et al. | |
| 7,442,181 B2 | 10/2008 | Schubert et al. | |
| 7,469,598 B2 | 12/2008 | Shkarlet et al. | |
| 7,469,599 B2 | 12/2008 | Froehlich et al. | |
| 7,470,266 B2 | 12/2008 | Massengale et al. | |
| 7,483,756 B2 | 1/2009 | Engleson et al. | |
| D588,200 S | 3/2009 | Langan et al. | |
| 7,534,239 B1 | 5/2009 | Schneider et al. | |
| D593,613 S | 6/2009 | Langan et al. | |
| D595,361 S | 6/2009 | Langan et al. | |
| 7,559,483 B2 | 7/2009 | Hickle et al. | |
| 7,564,579 B2 | 7/2009 | Tipirneni | |
| D597,608 S | 8/2009 | Langan et al. | |
| D602,534 S | 10/2009 | Langan et al. | |
| 7,614,545 B2 | 11/2009 | Christoffersen et al. | |
| 7,617,739 B1 | 11/2009 | Dam | |
| D605,228 S | 12/2009 | Langan et al. | |
| D605,229 S | 12/2009 | Langan et al. | |
| D605,230 S | 12/2009 | Langan et al. | |
| D607,941 S | 1/2010 | Langan et al. | |
| 7,645,258 B2 | 1/2010 | White et al. | |
| 7,673,527 B2 | 3/2010 | Ehring et al. | |
| 7,694,565 B2 | 4/2010 | Koerdt et al. | |
| 7,703,336 B2 | 4/2010 | Genosar | |
| 7,704,231 B2 | 4/2010 | Pongpairochana et al. | |
| 7,722,083 B2 | 5/2010 | McCarthy et al. | |
| 7,727,196 B2 | 6/2010 | Neer | |
| 7,753,880 B2 | 7/2010 | Malackowski | |
| 7,753,891 B2 | 7/2010 | Tennican et al. | |
| 7,756,724 B2 | 7/2010 | Gropper et al. | |
| 7,763,006 B2 | 7/2010 | Tennican | |
| D621,879 S | 8/2010 | Langan et al. | |
| D621,880 S | 8/2010 | Langan et al. | |
| 7,771,385 B2 | 8/2010 | Eggers et al. | |
| D624,595 S | 9/2010 | Langan et al. | |
| D624,596 S | 9/2010 | Langan et al. | |
| 7,799,010 B2 | 9/2010 | Tennican | |
| 7,813,939 B2 | 10/2010 | Clements et al. | |
| 7,815,123 B2 | 10/2010 | Conner et al. | |
| 7,815,605 B2 | 10/2010 | Souter | |
| 7,819,838 B2 | 10/2010 | Ziegler et al. | |
| 7,822,096 B2 | 10/2010 | Kuksenkov | |

(56) References Cited

U.S. PATENT DOCUMENTS

| | | |
|---|---|---|
| 7,834,816 B2 | 11/2010 | Marino et al. |
| 7,859,473 B2 | 12/2010 | Gibson |
| D633,151 S | 2/2011 | Langan et al. |
| 7,887,513 B2 | 2/2011 | Nemoto et al. |
| D634,367 S | 3/2011 | Langan et al. |
| D634,368 S | 3/2011 | Langan et al. |
| D634,369 S | 3/2011 | Langan et al. |
| 7,905,861 B2 | 3/2011 | Rhinehart et al. |
| 7,918,830 B2 | 4/2011 | Langan et al. |
| 7,922,073 B2 | 4/2011 | De La Huerga |
| 7,927,313 B2 | 4/2011 | Stewart et al. |
| 7,933,780 B2 | 4/2011 | De Le Huerga |
| 7,941,949 B2 | 5/2011 | Cloninger |
| D639,861 S | 6/2011 | Langan et al. |
| D639,862 S | 6/2011 | Langan et al. |
| D639,863 S | 6/2011 | Langan et al. |
| 7,967,778 B2 | 6/2011 | Nemoto et al. |
| D641,421 S | 7/2011 | Langan et al. |
| D641,422 S | 7/2011 | Langan et al. |
| 7,976,508 B2 | 7/2011 | Hoag |
| D643,468 S | 8/2011 | Langan et al. |
| D643,469 S | 8/2011 | Langan et al. |
| D643,470 S | 8/2011 | Langan et al. |
| D643,471 S | 8/2011 | Langan et al. |
| D643,472 S | 8/2011 | Langan et al. |
| D645,094 S | 8/2011 | Langan et al. |
| 7,991,627 B2 | 8/2011 | Hutchinson et al. |
| 8,031,347 B2 | 10/2011 | Edwards et al. |
| 8,035,517 B2 | 10/2011 | Gibson |
| D649,196 S | 11/2011 | Langan et al. |
| 8,059,297 B2 | 11/2011 | Tipirneni |
| 8,063,925 B2 | 11/2011 | Tainer et al. |
| 8,065,924 B2 | 11/2011 | Ziegler et al. |
| 8,069,060 B2 | 11/2011 | Tipirneni |
| 8,111,159 B2 | 2/2012 | Andreasson et al. |
| 8,133,178 B2 | 3/2012 | Brauker et al. |
| 8,140,349 B2 | 3/2012 | Hanson et al. |
| 8,151,835 B2 | 4/2012 | Khan et al. |
| 8,235,938 B2 | 8/2012 | Eggers et al. |
| 8,240,550 B2 | 8/2012 | Steusloff et al. |
| 8,303,547 B2 | 11/2012 | Brown |
| 8,328,082 B1 | 12/2012 | Bochenko et al. |
| 8,355,753 B2 | 1/2013 | Bochenko et al. |
| 8,385,972 B2 | 2/2013 | Bochenko et al. |
| 8,394,053 B2 | 3/2013 | Bochenko et al. |
| 8,480,834 B2 | 7/2013 | Rice et al. |
| 8,505,809 B2 | 8/2013 | Steusloff et al. |
| 8,606,596 B1 | 12/2013 | Bochenko et al. |
| 8,636,202 B2 | 1/2014 | Keefe et al. |
| 8,639,521 B2 | 1/2014 | Eggers et al. |
| 8,639,525 B2 | 1/2014 | Levine et al. |
| 8,645,154 B2 | 2/2014 | Eggers et al. |
| 8,702,674 B2 | 4/2014 | Bochenko |
| 8,752,088 B1 | 6/2014 | Harvey et al. |
| 9,216,440 B2 | 12/2015 | Ma et al. |
| 2001/0020148 A1 | 9/2001 | Sasse et al. |
| 2001/0049608 A1 | 12/2001 | Hochman |
| 2001/0056258 A1 | 12/2001 | Evans |
| 2002/0040208 A1 | 4/2002 | Flaherty et al. |
| 2002/0077852 A1 | 6/2002 | Ford et al. |
| 2002/0088131 A1 | 7/2002 | Baxa et al. |
| 2002/0098598 A1 | 7/2002 | Coffen et al. |
| 2002/0099334 A1 | 7/2002 | Hanson et al. |
| 2002/0161460 A1 | 10/2002 | Noguchi |
| 2002/0177811 A1 | 11/2002 | Reilly et al. |
| 2002/0188259 A1 | 12/2002 | Hickle et al. |
| 2003/0012701 A1 | 1/2003 | Sangha et al. |
| 2003/0052787 A1 | 3/2003 | Zerhusen et al. |
| 2003/0055685 A1 | 3/2003 | Cobb et al. |
| 2003/0065537 A1 | 4/2003 | Evans |
| 2003/0088238 A1 | 5/2003 | Poulsen et al. |
| 2003/0135388 A1 | 7/2003 | Martucci et al. |
| 2003/0139701 A1 | 7/2003 | White et al. |
| 2003/0139706 A1 | 7/2003 | Gray |
| 2003/0140929 A1 | 7/2003 | Wilkes et al. |
| 2003/0160698 A1 | 8/2003 | Andreasson et al. |
| 2003/0164401 A1 | 9/2003 | Andreasson et al. |
| 2003/0174326 A1 | 9/2003 | Rzasa et al. |
| 2003/0199897 A1 | 10/2003 | Boecker et al. |
| 2004/0051368 A1 | 3/2004 | Caputo et al. |
| 2004/0082918 A1 | 4/2004 | Evans et al. |
| 2004/0092885 A1 | 5/2004 | Duchon et al. |
| 2004/0103951 A1 | 6/2004 | Osborne et al. |
| 2004/0104271 A1 | 6/2004 | Martucci et al. |
| 2004/0105115 A1 | 6/2004 | Edwards et al. |
| 2004/0111078 A1 | 6/2004 | Miyahara |
| 2004/0179051 A1 | 9/2004 | Tainer et al. |
| 2004/0179132 A1 | 9/2004 | Fujino et al. |
| 2004/0186437 A1 | 9/2004 | Frenette et al. |
| 2004/0193453 A1 | 9/2004 | Butterfield et al. |
| 2004/0204673 A1 | 10/2004 | Flaherty |
| 2004/0212834 A1 | 10/2004 | Edwards et al. |
| 2004/0238631 A1 | 12/2004 | Andreasson et al. |
| 2005/0055242 A1 | 3/2005 | Bello et al. |
| 2005/0070978 A1 | 3/2005 | Bek et al. |
| 2005/0088306 A1 | 4/2005 | Andreasson et al. |
| 2005/0101905 A1 | 5/2005 | Merry |
| 2005/0106225 A1 | 5/2005 | Massengale et al. |
| 2005/0107923 A1 | 5/2005 | Vanderveen |
| 2005/0118048 A1 | 6/2005 | Traxinger |
| 2005/0151652 A1 | 7/2005 | Frasch |
| 2005/0151823 A1 | 7/2005 | Botten et al. |
| 2005/0154368 A1 | 7/2005 | Lim et al. |
| 2005/0165559 A1 | 7/2005 | Nelson |
| 2005/0182358 A1 | 8/2005 | Veit et al. |
| 2005/0277873 A1 | 12/2005 | Stewart et al. |
| 2005/0277890 A1 | 12/2005 | Stewart et al. |
| 2006/0032918 A1 | 2/2006 | Andreasson et al. |
| 2006/0065713 A1 | 3/2006 | Kingery |
| 2006/0079767 A1 | 4/2006 | Gibbs et al. |
| 2006/0079843 A1 | 4/2006 | Brooks et al. |
| 2006/0102503 A1 | 5/2006 | Elhadad et al. |
| 2006/0116639 A1 | 6/2006 | Russell |
| 2006/0122577 A1 | 6/2006 | Poulsen et al. |
| 2006/0143051 A1 | 6/2006 | Eggers et al. |
| 2006/0144942 A1 | 7/2006 | Evans et al. |
| 2006/0178617 A1 | 8/2006 | Adams et al. |
| 2006/0190302 A1 | 8/2006 | Eggers et al. |
| 2006/0206356 A1 | 9/2006 | Vanderveen |
| 2006/0224125 A1 | 10/2006 | Simpson et al. |
| 2006/0226089 A1 | 10/2006 | Robinson et al. |
| 2006/0229551 A1 | 10/2006 | Martinez et al. |
| 2006/0253346 A1 | 11/2006 | Gomez |
| 2006/0258985 A1 | 11/2006 | Russell |
| 2006/0265186 A1 | 11/2006 | Holland et al. |
| 2006/0270997 A1 | 11/2006 | Lim et al. |
| 2006/0287887 A1 | 12/2006 | Hutchinson et al. |
| 2007/0008399 A1 | 1/2007 | Botten et al. |
| 2007/0043335 A1 | 2/2007 | Olsen et al. |
| 2007/0100316 A1 | 5/2007 | Traxinger |
| 2007/0134044 A1 | 6/2007 | Colbrunn et al. |
| 2007/0135765 A1 | 6/2007 | Miller et al. |
| 2007/0136218 A1 | 6/2007 | Bauer et al. |
| 2007/0166198 A1 | 7/2007 | Sangha et al. |
| 2007/0167919 A1 | 7/2007 | Nemoto et al. |
| 2007/0179448 A1 | 8/2007 | Lim et al. |
| 2007/0186923 A1 | 8/2007 | Poutiatine et al. |
| 2007/0187475 A1 | 8/2007 | MacLeod |
| 2007/0191787 A1 | 8/2007 | Lim et al. |
| 2007/0255199 A1 | 11/2007 | Dewey |
| 2007/0279625 A1 | 12/2007 | Rzasa et al. |
| 2007/0280710 A1 | 12/2007 | Tainer et al. |
| 2007/0293830 A1 | 12/2007 | Martin |
| 2007/0299421 A1 | 12/2007 | Gibson |
| 2008/0043088 A1 | 2/2008 | Botten et al. |
| 2008/0045930 A1 | 2/2008 | Makin et al. |
| 2008/0051937 A1 | 2/2008 | Khan et al. |
| 2008/0061153 A1 | 3/2008 | Hickle et al. |
| 2008/0071219 A1 | 3/2008 | Rhinehart et al. |
| 2008/0118141 A1 | 5/2008 | Sommer et al. |
| 2008/0125724 A1* | 5/2008 | Monroe ............ A61C 1/0015 604/264 |
| 2008/0191013 A1 | 8/2008 | Liberatore |
| 2008/0208042 A1 | 8/2008 | Ortenzi et al. |

(56) References Cited

U.S. PATENT DOCUMENTS

| | | |
|---|---|---|
| 2008/0234630 A1 | 9/2008 | Iddan et al. |
| 2008/0243088 A1 | 10/2008 | Evans |
| 2008/0255523 A1 | 10/2008 | Grinberg |
| 2008/0294108 A1 | 11/2008 | Briones et al. |
| 2008/0306439 A1 | 12/2008 | Nelson et al. |
| 2009/0018494 A1 | 1/2009 | Nemoto et al. |
| 2009/0030730 A1 | 1/2009 | Dullemen et al. |
| 2009/0036846 A1 | 2/2009 | Dacquay et al. |
| 2009/0043253 A1 | 2/2009 | Podaima |
| 2009/0069714 A1 | 3/2009 | Eichmann et al. |
| 2009/0085768 A1 | 4/2009 | Patel et al. |
| 2009/0112178 A1 | 4/2009 | Behzadi |
| 2009/0112333 A1 | 4/2009 | Sahai |
| 2009/0126483 A1 | 5/2009 | Blendinger et al. |
| 2009/0126866 A1 | 5/2009 | Stenner et al. |
| 2009/0137956 A1 | 5/2009 | Souter |
| 2009/0143673 A1 | 6/2009 | Drost et al. |
| 2009/0149744 A1 | 6/2009 | Nemoto et al. |
| 2009/0156931 A1 | 6/2009 | Nemoto et al. |
| 2009/0157008 A1 | 6/2009 | Vitral |
| 2009/0159654 A1 | 6/2009 | Grimard |
| 2009/0200185 A1 | 8/2009 | Follman et al. |
| 2009/0259176 A1 | 10/2009 | Yairi |
| 2009/0288497 A1 | 11/2009 | Ziegler et al. |
| 2009/0294521 A1 | 12/2009 | De La Huerga |
| 2009/0296540 A1 | 12/2009 | Gilbert et al. |
| 2009/0306620 A1 | 12/2009 | Thilly et al. |
| 2010/0022953 A1 | 1/2010 | Bochenko et al. |
| 2010/0022987 A1 | 1/2010 | Bochenko et al. |
| 2010/0036310 A1 | 2/2010 | Hillman |
| 2010/0036313 A1 | 2/2010 | Shener et al. |
| 2010/0056975 A1 | 3/2010 | Dale et al. |
| 2010/0065633 A1 | 3/2010 | Nelson et al. |
| 2010/0065643 A1 | 3/2010 | Leyvraz et al. |
| 2010/0076310 A1 | 3/2010 | Wenderow et al. |
| 2010/0095782 A1 | 4/2010 | Ferencz et al. |
| 2010/0114951 A1 | 5/2010 | Bauman et al. |
| 2010/0140342 A1 | 6/2010 | Deshays |
| 2010/0145165 A1 | 6/2010 | Merry |
| 2010/0145721 A1 | 6/2010 | Deshays |
| 2010/0152562 A1 | 6/2010 | Goodnow et al. |
| 2010/0153136 A1 | 6/2010 | Whittacre et al. |
| 2010/0174266 A1 | 7/2010 | Estes |
| 2010/0179417 A1 | 7/2010 | Russo |
| 2010/0204659 A1 | 8/2010 | Bochenko et al. |
| 2010/0262002 A1 | 10/2010 | Martz |
| 2010/0280486 A1 | 11/2010 | Khair et al. |
| 2010/0286599 A1 | 11/2010 | Ziegler et al. |
| 2010/0305499 A1 | 12/2010 | Matsiev et al. |
| 2011/0009800 A1 | 1/2011 | Dam et al. |
| 2011/0009817 A1 | 1/2011 | Bennett et al. |
| 2011/0028937 A1 | 2/2011 | Powers et al. |
| 2011/0060198 A1 | 3/2011 | Bennett et al. |
| 2011/0093279 A1 | 4/2011 | Levine et al. |
| 2011/0111794 A1 | 4/2011 | Bochenko et al. |
| 2011/0112473 A1 | 4/2011 | Bochenko et al. |
| 2011/0112474 A1 | 4/2011 | Bochenko et al. |
| 2011/0137288 A1 | 6/2011 | Tallarida et al. |
| 2011/0152824 A1 | 6/2011 | DiPerna et al. |
| 2011/0152825 A1 | 6/2011 | Marggi |
| 2011/0152834 A1 | 6/2011 | Langan et al. |
| 2011/0160655 A1 | 6/2011 | Hanson et al. |
| 2011/0161112 A1 | 6/2011 | Keefe et al. |
| 2011/0166511 A1 | 7/2011 | Sharvit et al. |
| 2011/0176490 A1 | 7/2011 | Mehta et al. |
| 2011/0185821 A1 | 8/2011 | Genosar |
| 2011/0220713 A1 | 9/2011 | Cloninger |
| 2011/0224649 A1 | 9/2011 | Duane et al. |
| 2011/0259954 A1 | 10/2011 | Bartz et al. |
| 2011/0264069 A1 | 10/2011 | Bochenko |
| 2011/0284024 A1 | 11/2011 | Trebella et al. |
| 2011/0313349 A1 | 12/2011 | Krulevitch et al. |
| 2011/0315611 A1 | 12/2011 | Fulkerson et al. |
| 2012/0004542 A1 | 1/2012 | Nemoto et al. |
| 2012/0004602 A1 | 1/2012 | Hanson et al. |
| 2012/0004637 A1 | 1/2012 | Krulevitch et al. |
| 2012/0006127 A1 | 1/2012 | Nielsen |
| 2012/0022458 A1 | 1/2012 | Oh et al. |
| 2012/0035535 A1 | 2/2012 | Johnson et al. |
| 2012/0037266 A1 | 2/2012 | Bochenko |
| 2012/0041355 A1 | 2/2012 | Edman et al. |
| 2012/0046295 A1 | 2/2012 | Charrier et al. |
| 2012/0065617 A1 | 3/2012 | Matsiev et al. |
| 2012/0222468 A1 | 9/2012 | Nelson et al. |
| 2012/0226446 A1 | 9/2012 | Nelson et al. |
| 2012/0226447 A1 | 9/2012 | Nelson et al. |
| 2012/0287431 A1 | 11/2012 | Matsiev et al. |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0105568 A1 | 5/2013 | Jablonski et al. |
| 2013/0181046 A1 | 7/2013 | Fedorko et al. |
| 2013/0204227 A1 | 8/2013 | Bochenko et al. |
| 2013/0225945 A1 | 8/2013 | Prince et al. |
| 2013/0226137 A1 | 8/2013 | Brown |
| 2013/0327822 A1 | 12/2013 | Keefe et al. |
| 2014/0039383 A1 | 2/2014 | Dobbles et al. |
| 2014/0060729 A1 | 3/2014 | Smka et al. |
| 2014/0142975 A1 | 5/2014 | Keefe et al. |
| 2015/0204705 A1 | 7/2015 | Forster et al. |
| 2015/0211904 A1 | 7/2015 | Forster |

FOREIGN PATENT DOCUMENTS

| | | |
|---|---|---|
| GB | 2183046 A | 5/1987 |
| GB | 2504288 A | 1/2014 |
| GB | 2504295 A | 1/2014 |
| GB | 2504297 A | 1/2014 |
| WO | 2009114115 A1 | 9/2009 |
| WO | 2012034084 A2 | 3/2012 |
| WO | 2010144482 A2 | 12/2012 |
| WO | 2014016311 A1 | 1/2014 |
| WO | 2014016315 A1 | 1/2014 |
| WO | 2014016316 A1 | 1/2014 |

\* cited by examiner

US 9,931,498 B2

INJECTION SITE INFORMATION CAP

CROSS-REFERENCE TO RELATED APPLICATIONS

This application is a divisional application of U.S. Utility patent application Ser. No. 13/802,231 filed Mar. 13, 2013, the entire disclosure of which is herein incorporated by reference.

FIELD

The subject matter described herein relates to an injection site information cap and method for use in providing information to recordkeeping systems to automatically document caregiver identification, patient care activity, and/or procedural steps in the use of and/or care of a medication injection site.

BACKGROUND

Many health care procedures involve IV medication administrations. The type of medication and timing of administration are important to record in order to provide healthcare providers real-time information on the conduct of the procedure and the completion of a medical record. Some protocols require quick medication administrations with limited time for documentation and record keeping. Others require completion and verification of medication administration manually to ensure proper patient care and accounting for use of medications.

Injectable medications and fluids are frequently utilized by healthcare providers (caregivers) in the care of patients in the hospital, in pre-hospital emergency medical services (EMS) and at alternate care sites (including skilled nursing facilities, home health and hospice settings). Caregivers can include medical doctors, registered nurses, EMS paramedics, dentists and other licensed healthcare practitioners. Accurate documentation of what, when and how much medication and/or IV fluid is given to a patient is required by healthcare institutions, governmental agencies and regulatory oversight agencies. This is especially true when the IV fluid being administered to the patient is a medication or blood product. The type of IV fluid and the timing of administration are important to record in order to provide healthcare providers real-time information on the conduct of the procedure and the completion of a medical record. Some protocols require quick IV fluid administrations with limited time for documentation and record keeping. Others require completion and verification of manually administered IV fluids to ensure proper patient care and accounting for use of IV fluids.

Additionally, to ensure proper patient safety and limit exposure to catheter-related bloodstream infections (CRBSI), vascular access ports (injection sites) require careful disinfection and careful management of the patient's IV site for patency. Absent these activities, needleless injection sites can become contaminated and patient vascular access can become infiltrated or blocked. When these situations occur, patient safety is compromised resulting in infection, pain, longer hospital stays and even death. Hospital costs for continued patient care increase and are not reimbursed by third party payers.

New automated documentation systems for medication administrations will likely help in the tracking of medication injections, but none have addressed the documentation of proper IV site care and the management of needleless injection sites for infection control or IV site for patency. Manual use of alcohol swabs or sterile caps containing a disinfectant solution are gaining popularity for disinfecting IV injection sites and controlling CRBSI. When caps are left attached to IV luer access needleless valves they can disinfect and protect the IV site. To date, these activities are often not documented, rarely time tracked and even less likely to be identified by caregiver.

Other patient care activity and procedural steps such as obtaining lab samples, assisting in respiratory therapy, dietary management also require timely documentation. Manual documentation often results in accuracy errors, missed notations and undocumented activity due to fast paced patient care with limited resources. A better system could result in less error, increased billing accuracy, reduced paperwork and more time for caregivers to focus on patient care. Tracking of who did what and when at the point of care can be improved.

SUMMARY

In one aspect, an injection site information cap includes a housing, a cover portion, an engagement portion configured to couple to and cover an injection port of an injection site and at least one information element on the cover portion that is positioned to be automatically sensed by at least one sensor of the injection site when the engagement portion is coupled to or is being coupled to the medication injection port.

The engagement portion can include a female luer lock thread configured to be coupled to a male luer lock thread on the injection port.

The at least one information element can be encoded with one or more of: mechanically encoded information, magnetically encoded information, a near field communication (NFC) tag, and a radio frequency identification (RFID) tag.

The at least one information element can include optically encoded information. The optically encoded information can include at least one bar code. The at least one bar code can be sensed by the at least one sensor as the cover portion is circumferentially rotated or translated linearly on the axial centerline of the luer lock.

The injection site information cap can include a disinfectant to disinfect the injection port upon the coupling of the engagement portion with the injection port. The engagement portion can be further configured to seal the injection port of the injection site.

The injection port can be fluidically coupled to a patient and/or to a fluid wasting reservoir.

The information element can encapsulate data characterizing one or more of: a disinfection state of the injection port, a caregiver identification, an identification of a patient, a procedural step performed in connection with care of the patient, a state of waste disposal, a lab sample, respiratory management for the patient, and dietary management for the patient.

Some or all of the housing can be color coded with one of a plurality of color categories. Each color category can characterize one or more of: caregiver identification, a patient care procedural activity, a laboratory sample, a state of the injection port, a fluid injected into the injection port, and a state of a patient. The at least one sensor or a different sensor can, in some variations, detect the color. In addition, in some variations, at least the information element is color coded with one of a plurality of color categories, each color category characterizing one or more of: care giver identification, a patient care procedural activity, a laboratory sample, a state of the injection port, a fluid injected into the injection port, and a state of a patient.

The information element can be affixed to an outer surface of the cover portion or it can be integral to an outer surface of the cover portion.

In a further aspect, an injection site information cap can include multiple engagement portions. For example, a medication injection site can comprise a housing including a first engagement portion on the housing configured to couple to and cover a first injection port of a first injection site. At least one first information element on an outer surface of the first engagement portion of the housing can be positioned to be automatically sensed by at least one first sensor of the first injection site when the first engagement portion is coupled to or is being coupled to the first injection port, a second engagement portion on the housing can be configured to couple to and cover a second injection port of a second injection site, and at least one second information element on an outer surface of the second engagement portion of the housing can be positioned to be automatically sensed by at least one second sensor of the second injection site when the second engagement portion is coupled to or is being coupled to the second injection port.

The at least one of the first engagement portion and the second engagement portion can comprises a female luer lock thread configured to couple to a male luer lock thread on the injection port. The at least one first information element and the at least one second information element can be encoded with one or more of: mechanically encoded information, magnetically encoded information, a near field communication (NFC) tag, and a radio frequency identification (RFID) tag. The at least one second information element can be optically encoded information. The optically encoded information can be at least one bar code. The at least one bar code can be sensed by the at least one sensor as the housing is circumferentially rotated.

The information cap can further comprise: a disinfectant to disinfect at least one of the first injection port upon the coupling of the first engagement portion to the first injection port. The at least one of the first injection port and the second injection port can be fluidically coupled to a patient. The at least one of the first injection port and the second injection port can be fluidically coupled to a fluid wasting reservoir.

The injection site information cap can include one or more of the at least one first information element and the at least one second information element to encapsulate data characterizing one or more of: a disinfection state of the injection port, a caregiver identification, an identification of a patient, a procedural step performed in connection with care of the patient, a state of waste disposal, a lab sample, respiratory management for the patient, and dietary management for the patient. The information cap can include at least a portion of the housing, and/or the information element, to be color coded with one of a plurality of color categories, each color category characterizing one or more of: caregiver identification, a patient care procedural activity, a laboratory sample, a state of the injection port, a fluid injected into the injection port, and a state of a patient.

The one or more of the at least one first information element and the at least one second information element can be affixed to an outer surface of the housing. The at least one first information element and the at least one second information element can be integral to an outer surface of the housing. The at least one of the first engagement portion and the second engagement portion can be further configured to seal and/or cover the injection port of the injection site. The first injection site and the second injection site can be physically connected to each other.

In some variations, the at least one first information element is different from the at least one second information element while in other variations the elements are the same (identical). Each engagement portion can have identical features such as disinfectant or they can differ (one side has disinfectant while the other does not). The housing can be color coded in different manners similar to a single engagement portion injection cap.

The first engagement portion can be positioned opposite the second engagement portion. In other variations, the first engagement portion is positioned at an angle or otherwise askew as compared to a center line of the second engagement portion. In other variations, the housing can be flexible.

In a further interrelated aspect, an apparatus includes a first engagement portion on the housing configured to cover a injection port, at least one first information element on an outer surface of the first engagement portion of the housing positioned to be automatically sensed by at least one first sensor of the injection site when the first engagement portion is coupled to or is being coupled to the injection port; a second engagement portion on the housing configured to cover the injection port, and at least one second information element on an outer surface of the second engagement portion of the housing positioned to be automatically sensed by at least one sensor of the injection site when the second engagement portion is coupled to or is being coupled to the injection port.

The injection site information caps as described herein can be used in connection with various methods. For example, one method can include receiving information from a medication delivery apparatus characterizing at least one information element on a cap covering an injection port of the medication delivery apparatus, associating the received information with data comprising one or more of: a disinfection state of the injection port, a caregiver identification, an identification of a patient, a procedural step performed in connection with care of the patient, a state of waste disposal, a lab sample, respiratory management for the patient, and dietary management for the patient, and promoting the associated data.

The medication delivery apparatus (injection site) can include a housing, a fluid conduit at least partially extending within the housing and configured to deliver medication within a medication container to the patient, an injection port extending from an external surface of the housing and configured to be coupled to a fluid outlet of the medication container (the medication port being fluidically and directly coupled to the fluid conduit), and at least one sensor disposed within the housing to sense the at least one information element on the information cap. In some variations, the medication delivery apparatus can also include a transmitter within the housing to wirelessly transmit information generated by the at least one sensor to a remote data collection system, and a self-contained power source within the housing powering the at least one sensor and the transmitter.

Promoting the associated data can include one or more of: displaying the associated data, storing the associated data into a physical storage device, loading the associated data into memory, and transmitting the associated data to a remote computing system.

Computer program products are also described that comprise nontransitory computer readable media storing instructions, which when executed one or more data processor of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter allows for compact injection port systems that automatically identify activity at the injection site. The fluid injection port is sufficiently small to be placed on a standard IV line (and to be self-supporting) allowing it to be used in multiple situations including on-site paramedic treatments, during ambulance delivery of patients, as well as medical facilities such as emergency rooms/intensive care units/operating rooms/general care. Moreover, as medical staff (e.g., doctors, nurses, paramedics, etc.) are accustomed to handling Y-sites on IV lines and the current subject matter requires little, if any, behavior modifications while allowing for intelligent logging of patient care activities within normal workflow. In addition, the compact nature of the fluid injection port obviates the need for a larger tabletop or cradle bar code unit which can be cumbersome during code blue or other emergency events and which can require much needed space (displacing other required equipment). In addition, the current subject matter utilizes a wireless interface and does not require wires for communication of information to a data collection system which could interfere with or complicate patient care activity. Data received by the data collection system can be actively displayed in real-time providing clearly visible information to the medical staff keeping all informed and up-to-date. Furthermore, the current subject matter reduces manual record keeping and other activities that can tend to detract from the needed attention to a patient. Automated record keeping provides accurate records and frees up the health care provider's time enabling improved patient care.

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

Like reference symbols in the various drawings indicate like or similar elements.

DETAILED DESCRIPTION

This application relates to each of the following applications, which are all entitled "Medication Injection Site and Data Collection System": U.S. patent application Ser. No. 13/777,964 filed Feb. 26, 2013, which is a continuation-in-part of U.S. patent application Ser. No. 13/777,831 filed on Feb. 26, 2013, which in turn is a continuation-in-part of U.S. patent application Ser. No. 12/938,300 filed on Nov. 2, 2010, which in turn is a continuation-in-part of U.S. patent application Ser. No. 12/765,707 filed on Apr. 22, 2010, which in turn is a continuation-in-part of U.S. patent application Ser. No. 12/614,276 filed on Nov. 6, 2009; and additionally, priority is also claimed to U.S. patent application Ser. No. 61/370,974 filed on Aug. 5, 2010. Each of the aforementioned patent applications are hereby fully incorporated by reference.

Additionally, this application relates to each of the following applications, which are entitled "Medication Container Encoding, Verification, and Identification": U.S. patent application Ser. No. 13/671,752 filed Nov. 8, 2012, which is a continuation-in-part of U.S. patent application Ser. No. 13/149,782 filed on May 31, 2011. Each of the aforementioned patent applications are hereby fully incorporated by reference.

Figure 1:
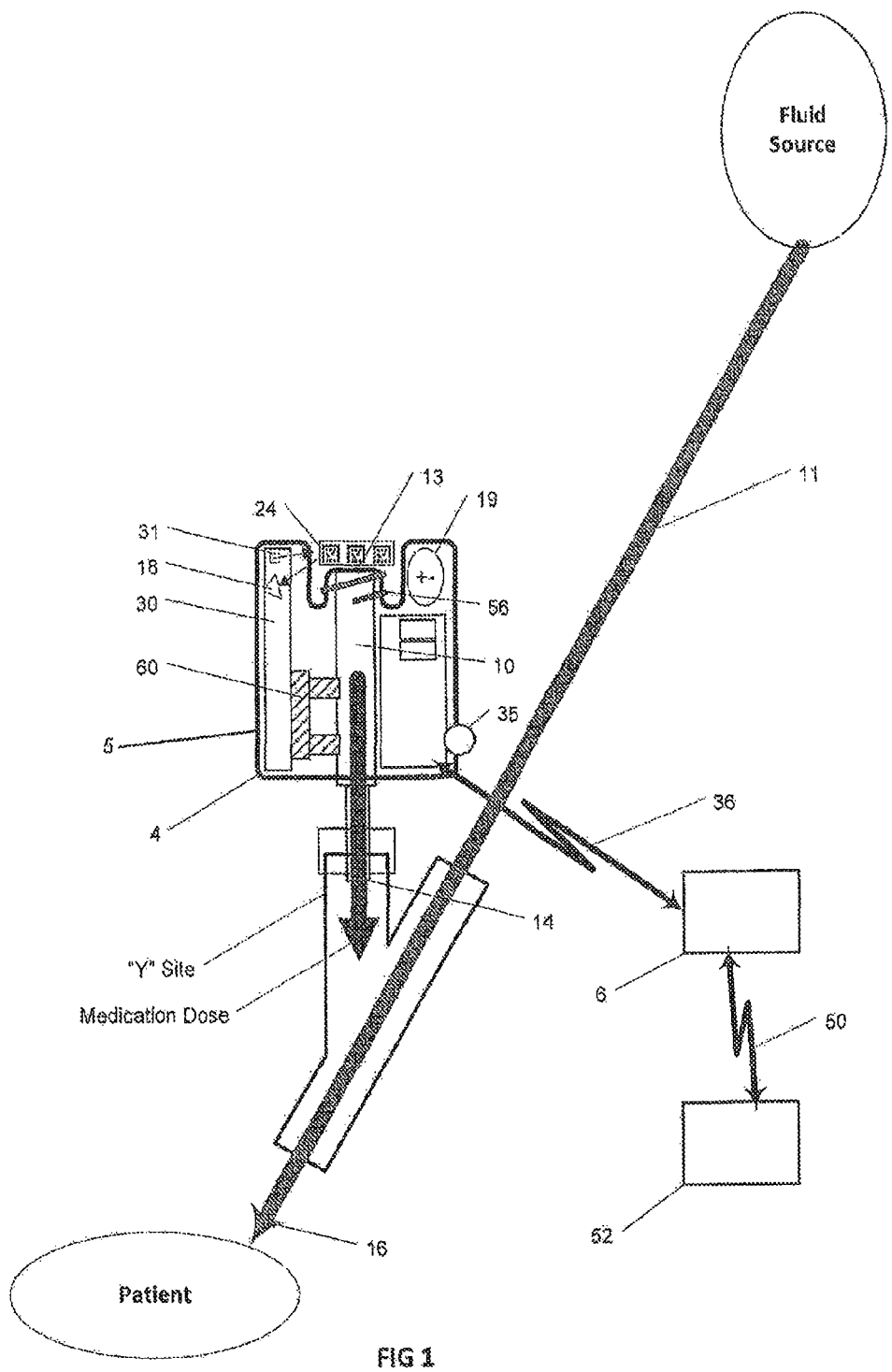
FIG. 1 depicts an intelligent injection site housing directly coupled to a "Y" site of an IV fluid delivery tubing set.

FIG. 1 depicts an intelligent injection site 4 directly coupled to a "Y" site of an IV fluid delivery tubing set 11. Connection of an intelligent injection site can be to other injection sites such as stopcocks, manifolds, "T" sites, venous access devices, catheters, etc. Details of intelligent injection site 4 are discussed in the referenced patent applications entitled "Medication Injection Site and Data Collection System". Tubing set 11 is attached at one end to a fluid source for delivery of fluids to a patient. Distal end of tubing set 11 is attached to vascular access device 16 (needle, catheter, etc.). Located in between each end of tubing set 11 is a "Y" site providing and injection site for additional fluids and medications to be administered to a patient. Fluid containers can be coupled to intelligent injection site 4 by inlet 13 and luer lock threads 56. Outlet 14 of intelligent injection site 4 can be coupled to the "Y" site providing for fluid delivery to a patient into inlet 13, through conduit 10 and out of output 14. Intelligent injection site 4 can include emitter 31 and identification sensor 18 positioned such that when an information element 24 is in the field of view or within a predefined distance, circuit 30 can image and transmit 36 information contained on information element 24 to data collection system 6. Data collection system 6 can transmit 50 data collected to medical information system 52. Additionally, intelligent injection site 4 can include fluid delivery sensor 60, power source 19 and indicator 35.

Figure 2:
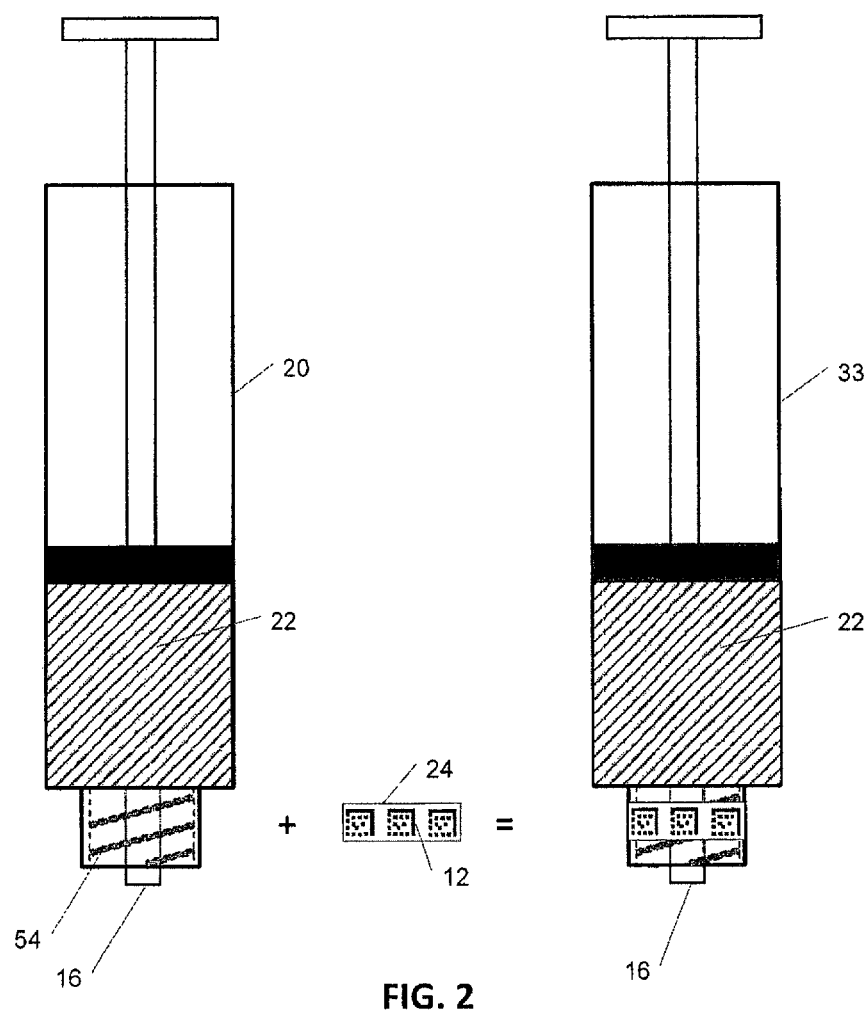
FIG. 2 depicts a medication container with an information element attached.

FIG. 2 depicts a medication container 20 (syringe example) with an added information element 24 forming an encoded medication container 33. Information element 24 can be a label for example and can contain encoded information 12. Encoded medication container 33 can contain medication 22 for injection into a medication injection site. Medication container 33 can include outlet 16 to deliver medication 22 to a medication injection site. Details of information element 24 and its coupling to medication container 33 are discussed in the referenced patent applications entitled "Medication Container Encoding, Verification, and Identification".

Figure 3:
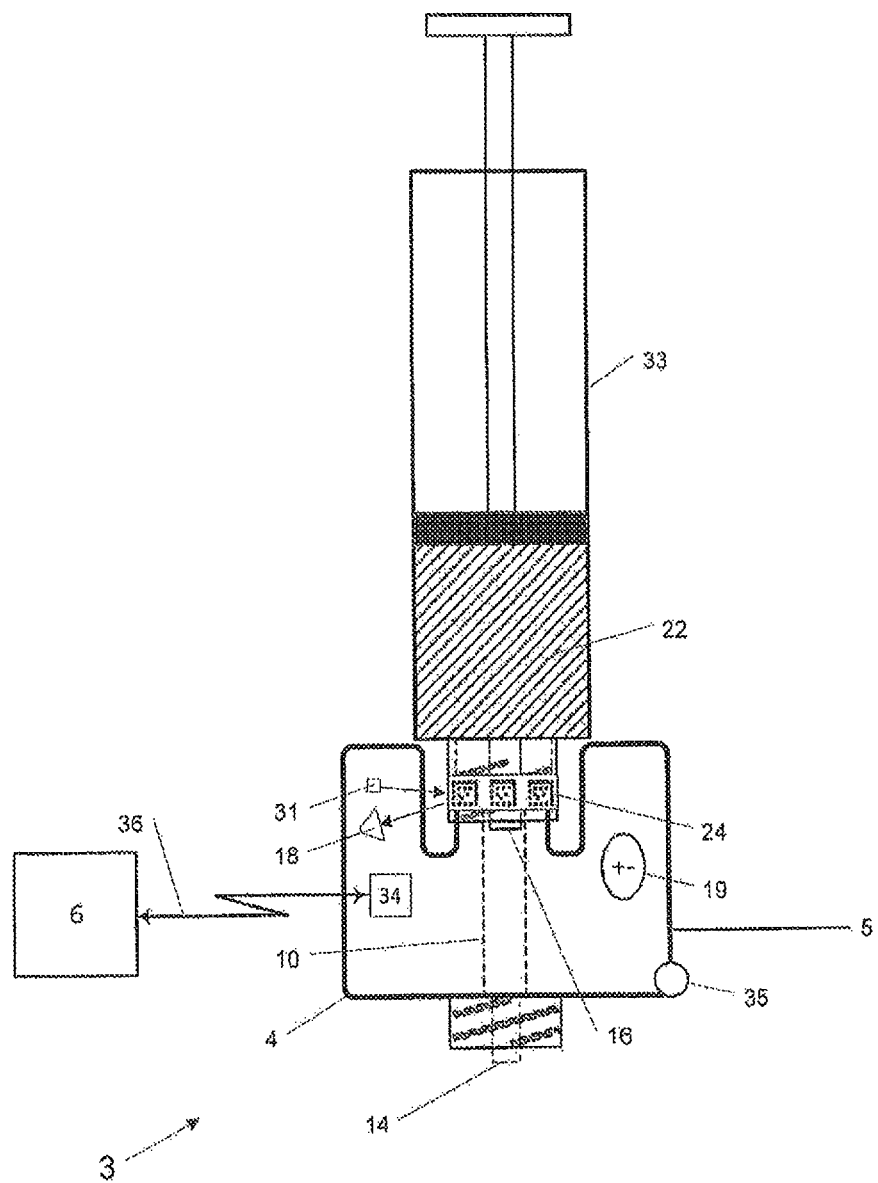
FIG. 3 illustrates a medication container attached to an intelligent injection site housing.

FIG. 3 illustrates system 3 with an encoded medication container 33 attached to housing 5 of an intelligent injection site 4. Fluid outlet 16 of medication container 33 can be coupled to fluid inlet 13 of intelligent injection site 4. Coupling can automatically activate emitter 31 and identification sensor 18 to read information element 24. Data from information element 24 can be transmitted 36 by transmitter 34 to data collection system 6. Data collection system 6 can identify, display, time stamp and record the information content of information element 24. Medication container 33 can expel medication 22 through conduit 10, through outlet 14 and into an injection site coupled to a patient. Fluid delivery sensor 60 (not shown) can measure the expelled fluid 22 and transmit 36 data to data collection system 6. Data collection system 6 can display, time stamp and record the data from fluid delivery sensor 60.

Figure 4:
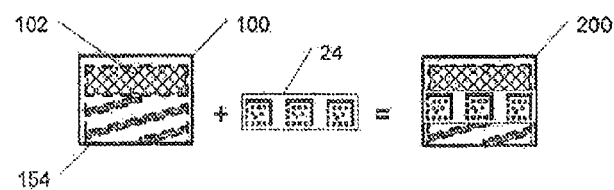
FIG. 4 depicts an injection site information cap with an information element attached.

FIG. 4 depicts an injection site cap 100 that can include information element 24 forming information cap 200. The injection site information cap 200 can have a shape and size configured to couple to and cover (and in some cases seal) an injection port. Injection site information cap 200 can include luer lock threads 154 on the inner diameter. Additionally, injection site information cap 200 can include a disinfectant 102 to disinfect an injection site ("Y" site) on IV tubing set 11 as shown in FIG. 1. Disinfectant 102 can be 70% alcohol or any other type of IV site disinfectant. Injection site information cap 200 can limit contact with injection site 4 fluid inlet 13 to only the surface of housing 5 (fluid inlet surface 13 and/or external threads 56) and not enter the fluid pathway.

Figure 5:
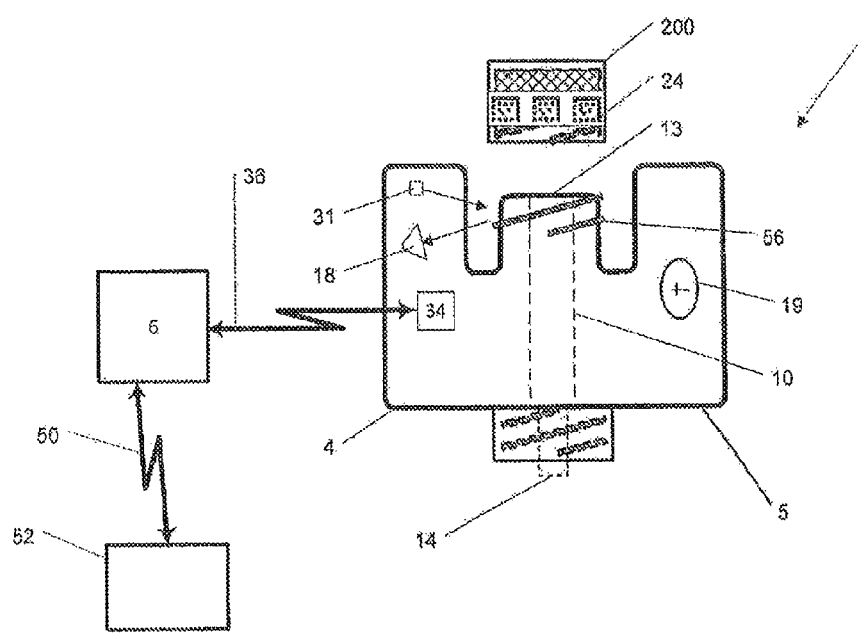
FIG. 5 depicts an information cap about to be attached to intelligent injection site.

In addition to system 3 for encoded medication containers as shown in FIG. 3, FIG. 5 depicts a non-medication container information system 2. System 2 can include information element 24, information cap 200, intelligent injection site 4 and data collection system 6. Information cap 200 can be made from plastic (polycarbonate, polystyrene, polyvinylchloride, etc.), can be provided sterile and can be enclosed in a sealed foil package for single use. Information cap 200 can attach to inlet 13 by engaging internal luer lock threads 154 with external threads 56 on intelligent injection site 4. Information cap 200 can be rotated clockwise to engage luer lock threads 154 and 56. Information cap 200 can be rotated counter clockwise to disengage luer lock threads 154 and 56 and remove information cap 200. Information cap 200 can be a push-on type without luer lock threads 154. Information cap 200 can cover, protect and/or disinfect inlet 13.

Information cap 200 can be colored to designate a category. The color can be part of housing 5, part of information element 24 (background color) or part of data element 12. Categories can include any assigned color or type. For example color assignments could be: red=lab sample taken, orange=caregiver ID, yellow=medication given, green=billing charge, blue=physical therapy activity, violet=lab sample taken, white=sedation activity. Other colors and/or categories can be included. The color can be detected by identification sensor 18 and transmitted to the data collection system in addition to the information contained in the information element. The information can be detected by identification sensor 18 when a specific wavelength light (ultraviolet, infrared, etc), a specific RF or magnetic frequency, or a combination of frequency and wavelength is emitted from emitter 31.

Information cap 200 can be used with intelligent injection site 4 for caregiver identification during medication waste disposal. In this use case, intelligent injection site 4 can be connected to a medication waste disposal receptacle. Information cap 200 can contain caregiver ID information and document who and when medication waste is disposed. This can be followed by an encoded medication container and injection of waste medication into the receptacle. Fluid delivery sensor 60 can measure the volume of waste disposed. A second caregiver can verify waste disposal by immediately following waste disposal with the attachment of a second information cap 200 having a different caregiver ID. Information detected on caregivers information caps 200 and encoded medication container waste disposed volume can be transmitted 36 to data collection system 6, time stamped and transmitted 50 to medical information system 52.

Figure 6:
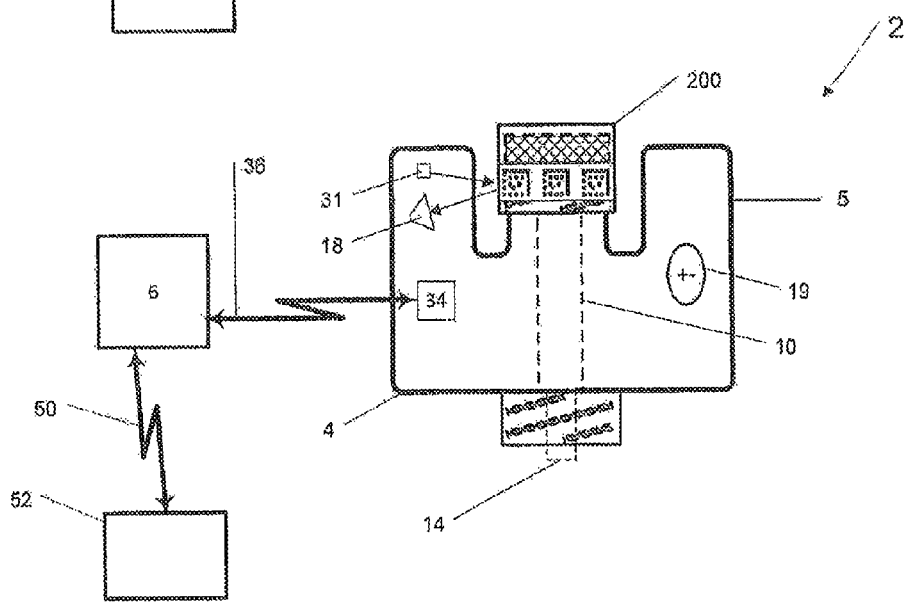
FIG. 6 illustrates an information cap fully coupled to an intelligent injection site.

FIG. 6 illustrates system 2 with information cap 200 fully coupled to intelligent injection site 4. Coupling information cap 200 to intelligent injection site 4 can automatically activate emitter 31 and identification sensor 18 to read information element 24. Data from information element 24 can be transmitted 36 by transmitter 34 to data collection system 6. Data collection system 6 can identify, display, time stamp and record the information content of information element 24. Data collection system 6 can display, time stamp and record the data from identification sensor 18. Data collection system 6 can transmit 50 this data to medical information system 52.

Information element 24 on information cap 200 can be any one or more of: mechanically encoded information, magnetically encoded information, a near field communication (NFC) tag, a radio frequency readable information (RFID tag). The information element 24 can also or alternatively comprise optically encoded information and the identification sensor 18 can comprise an optical emitter and an optical detector to read the optically encoded information. The identification sensor 18 can include an optical emitter LED to illuminate the information element 24 and an optical detector such as a camera (charge coupled device—CCD). The identification sensor 18 can read information from the information element 24 as a result of relative motion of the information cap relative to injection site 4. The identification sensor 18 can read information from the information element 24 in response to mechanically coupling the information cap 200 to the injection site 4.

Information cap 200 can carry an information element 24 that provides detectable information indicative of an activity performed by a caregiver or a patient. The activity can be any one or more of: disinfection of the injection site, caregiver identification (name, ID number, employee number), a procedural step performed (IV site visual assessment, a surgical procedure step, an intensive care unit activity, an emergency medical services {EMS} activity), confirmation of waste disposal (unused controlled substances, contaminated waste, etc.), other patient care activity such as obtaining a lab sample from a patient, assisting in respiratory therapy of a patient, dietary management of a patient, and many other patient care activities at home, in the field, or in a hospital environment where recordation is appropriate. The data encapsulated by element 24 can be detected by an intelligent injection site and processed either locally or by transmitting to a remote computing system.

The identification sensor 18 can include an optical emitter/detector pair 31 that detects encoded information contained on information element 24 (a sleeve or label wrapped around injection site information cap 100). The identification sensor 18 can comprise a plurality of sensors to detect information element 24. In some variations, the identification sensors can be sensors such as optical, magnetic, mechanical, conductive, switchable RFID and/or proximity sensors. In other variations, identification sensor 18 can be optical and can include an illumination source (emitter) such as an LED and a detection source (detector) such as a camera (CCD). Sensor circuit 30 can provide signal processing and connects identification sensor 18 to transmitter 34. The identification sensor 18 can be directly coupled to power source 19.

Figure 7:
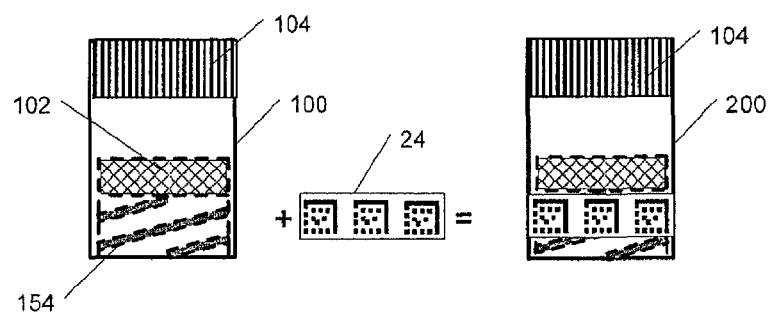
FIGS. 7 & 8 illustrate two alternative information caps with extended surfaces.
Figure 8:
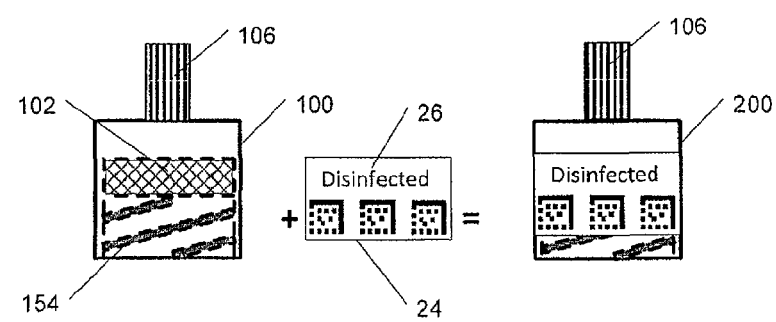

FIGS. 7 & 8 illustrate two alternative information caps 200 with extended surfaces to assist users in attaching and detaching information cap 200 from/to injection site 4. FIG. 7 illustrates an extended cap housing with a stripped grip section 104. FIG. 8 illustrates a narrower extended surface 106 forming a finger grip handle. Additionally, information element 24 can include human readable information 26 ("Disinfected") to enable a user to verify the information content prior to information cap 200 use.

Figure 9:
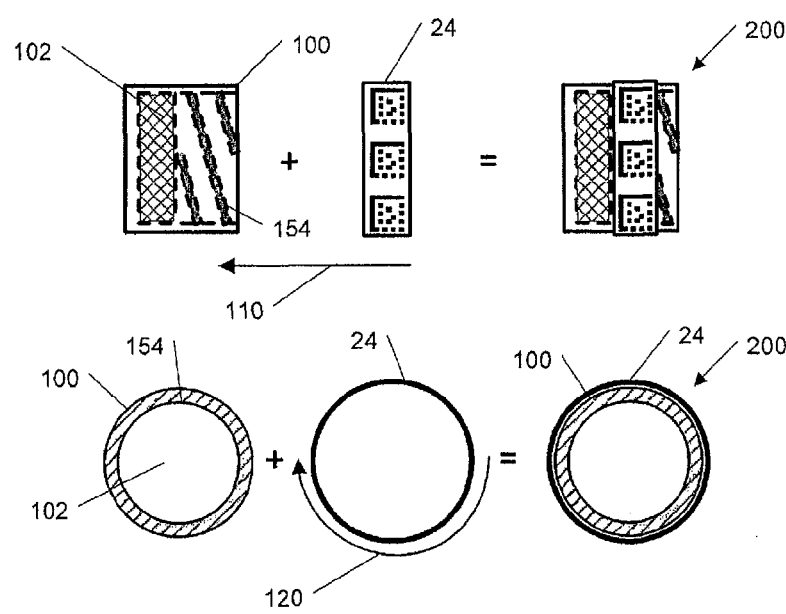
FIG. 9 illustrates two alternatives of applying an information element to an injection site information cap.

FIG. 9 illustrates two alternatives of applying information element 24 to injection site cap 100. As shown at the top, information element 24 can slide over (110) and attach to injection site cap 100 forming assembled information cap 200. On the bottom, information element 24 can wrap around (120) and attach to injection site cap 100 forming assembled information cap 200. Information element 24 can be a label or any one of: an optical image (1 dimensional barcode, 2 dimensional barcode, symbol, image or picture), a magnetic image (magnetic strip on an identification card/badge/ID tag), a Near Field Communication (NFC) tag, an RFID tag, and/or mechanically encoded information. Details are included in aforementioned patent applications.

Figure 10:
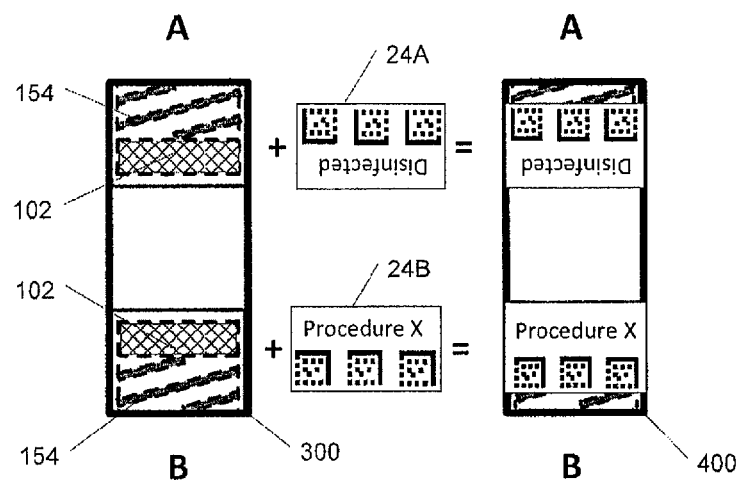
FIG. 10 illustrates a double ended information cap.

FIG. 10 depicts an information cap 400 with two active ends (A and B). Injection site cap 300 can have two ends A and B. Each end can have disinfectant 102 and luer lock threads 154. Injection site cap 300 can have two information elements (24A and 24B), one at each end to form injection site information cap 400. Information element 24A can be the same as information element 24B to allow multiple uses (e.g. two injection site disinfections). Information element 24A can be different from information element 24B allowing two different activities to be recorded. One could be "Disinfected" (24A) and the other could be a procedural step "Procedure X" (24B). The sequence and timing of use can be determined by the user. For example: End A can be used prior to a medication injection to provide information 24A (disinfection of the injection site). A medication can then be administered using an encoded syringe (see FIG. 3). End B can be used to provide information 24B (document the procedural step "X"). End B can remain coupled to the intelligent injection site 4 to protect it from contamination. The data collection system 6 can record and timestamp each information element (24A and 24B) as well as the medication administration. Maintaining End B coupled to the injection site can be recorded by the data collection system ("site protected", End B=not removed). At a later time, when End B is removed from the injection site, the injection site can be recorded as unprotected. This same recordation can be completed using single ended information cap 200. It will be appreciated that information cap 400 can have more than two active ends. In some variations, the housing of information cap 400 can be flexible and optionally elongated.

Figure 11:
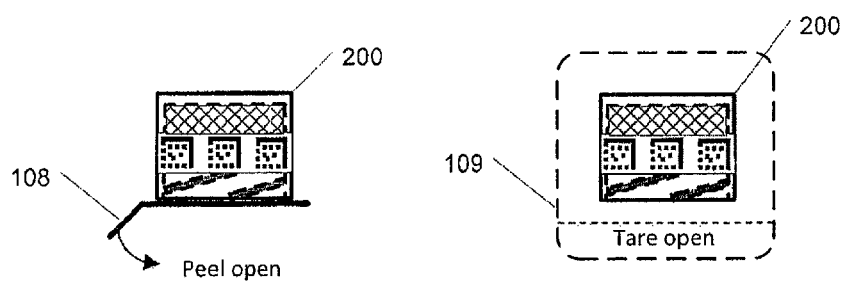
FIG. 11 illustrates several possible packaging configurations.

FIG. 11 illustrates two methods of packaging and sealing the open end of information cap 200 (or 400). To the left is a simple peel open tab foil/poly seal 108. To the right is a foil/poly sealed pouch 109 with a tare open strip. Any number of other methods of packaging and sealing information cap 200 can be envisioned. Each method can protect information cap 200 internally prior to use, maintain sterility and contain the disinfectant solution.

Aspects of the subject matter described herein can be embodied in systems, apparatus, kits (e.g., kits with the medication injection site being enclosed therein), methods, and/or articles depending on the desired configuration. In particular, aspects of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method comprising:
coupling a cap provided with at least one first information element to an injection port of an injection site including a fluid pathway within a housing such that the cap fluidically seals and covers the injection port without entering the fluid pathway, the cap comprising a disinfectant for disinfecting the injection site;
automatically sensing, with at least one sensor within the housing in response to the coupling of the cap, first information from the at least one first information element, wherein the first information is associated with a caregiver identification;
coupling a medication container provided with at least one second information element to the injection port of the injection site;
automatically sensing, with the at least one sensor in response to the coupling of the medication container, second information from the at least one second information element, wherein the second information is associated with a medication in the medication container;
receiving and processing, by at least one data processor, the first information and the second information, with data comprising at least a disinfection state of the injection port; and
promoting the processed data, wherein promoting the processed data comprises at least one of: displaying the processed data, storing the processed data into a physical storage device, loading the processed data into memory, and transmitting the processed data to a remote computing system.

2. The method as in claim 1, further comprising:
wirelessly transmitting, with a transmitter within the housing, the first information and the second information to wirelessly transmit information generated by the at least one sensor to a remote data collection system; and
powering, with a self-contained power source within the housing, the at least one sensor and the transmitter.

3. The method as in claim 1, wherein the first information received and processed from the at least one first information element further comprises data including at least one of: an identification of a patient, a procedural step performed in connection with care of the patient, a state of waste disposal, a lab sample, respiratory management for the patient, and dietary management for the patient.

4. The method as in claim 1, further comprising time-stamping the first information and the second information.

5. The method as in claim 1, further comprising:
expelling, from the medication container, the medication from the medication container through the fluid pathway within the housing;
sensing, with the at least one sensor within the housing, a volume of the medication expelled through the fluid pathway; and
receiving and processing, by the at least one data processor, the first information and the second information, with data comprising at least the volume of the medication expelled through the fluid pathway.

6. A method comprising:
coupling an injection site including a fluid pathway within a housing to a fluid wasting reservoir;
coupling a first cap provided with a first information element to an injection port of the injection site;
automatically sensing, with an identification sensor within the housing in response to the coupling of the first cap, first information from the first information element, wherein the first information is associated with a first caregiver identification of a first caregiver;
coupling a medication container provided with a second information element to the injection port of the injection site;
automatically sensing, with the identification sensor in response to the coupling of the medication container, second information from the second information element, wherein the second information is associated with a medication in the medication container;
expelling the medication from the medication container through the fluid pathway within the housing to the fluid wasting reservoir;
automatically sensing, with a fluid sensor within the housing, a volume of the medication expelled through the fluid pathway;
coupling a second cap provided with a third information element to the injection port of the injection site;
automatically sensing, with the identification sensor in response to the coupling of the second cap, third information from the third information element, wherein the third information is associated with a second caregiver identification of a second caregiver different than the first caregiver identification of the first caregiver;

receiving and processing, by at least one data processor, the first information, the second information, and the third information, with data associated with a state of waste disposal of the medication; and promoting the processed data, wherein promoting the processed data comprises at least one of: displaying the processed data, storing the processed data into a physical storage device, loading the processed data into memory, and transmitting the processed data to a remote computing system.

7. A method comprising:

coupling a first end of a cap provided with a first information element to an injection port of an injection site including a fluid pathway within a housing, wherein the cap comprises the first end and a second end opposite the first end, wherein the first information element is provided at the first end of the cap, and wherein a second information element is provided at the second end of the cap opposite the first end, and wherein the cap comprises a disinfectant for disinfecting the injection site;

automatically sensing, with an identification sensor within the housing in response to the coupling of the first end of the cap, first information from the first information element;

coupling the second end of the cap provided with the second information element to the injection port of the injection site;

automatically sensing, with the identification sensor in response to the coupling of the second end of the cap, second information from the second information element;

receiving and processing, by at least one data processor, the first information and the second information, with data comprising at least the disinfection state of the injection port; and promoting the processed data, wherein promoting the processed data comprises at least one of: displaying the processed data, storing the processed data into a physical storage device, loading the processed data into memory, and transmitting the processed data to a remote computing system.

8. The method as in claim 7, wherein the first information is associated with a disinfection state of the injection site, and wherein the second information is associated with at least one of: a caregiver identification, an identification of a patient, a procedural step performed in connection with care of the patient, a state of waste disposal, a lab sample, respiratory management for the patient, dietary management for the patient, or any combination thereof.

9. The method as in claim 8, further comprising:

coupling a medication container provided with a third information element to the injection port of the injection site;

automatically sensing, with the identification sensor in response to the coupling of the medication container, third information from the third information element, wherein the third information is associated with a medication in the medication container; and receiving and processing, by at least one data processor, the first information, the second information, and the third information, with the data comprising at least the disinfection state of the injection port.

10. The method as in claim 9, wherein the first end of the cap is coupled to the injection port of the injection site before coupling the medication container to the injection port of the injection site, and wherein the second end of the cap is coupled to the injection port of the injection site after coupling the medication container to the injection port of the injection site.

* * * * *